United States Patent [19]

Farooq et al.

[11] 3,998,972
[45] Dec. 21, 1976

[54] DIPHENYL DERIVATIVES
[75] Inventors: Saleem Farooq, Aesch; Friedrich Karrer, Basel, Switzerland
[73] Assignee: Ciba-Geigy Corporation, Ardsley, N.Y.
[22] Filed: Oct. 3, 1975
[21] Appl. No.: 619,416
[30] Foreign Application Priority Data
Sept. 3, 1975 Switzerland .................. 11408/75
[52] U.S. Cl. .................. 424/337; 260/571; 260/573; 260/609 F; 424/340; 424/330
[51] Int. Cl.² .................. C07C 149/32; A01N 9/00
[58] Field of Search .................. 260/609 F; 424/337
[56] References Cited
UNITED STATES PATENTS

| | | | |
|---|---|---|---|
| 2,299,213 | 10/1942 | Crok | 260/609 F |
| 2,655,544 | 10/1953 | McNulty et al. | 260/609 F |
| 3,718,686 | 2/1973 | Chodnekar et al. | 60/609 F |
| 3,914,321 | 10/1975 | Pallos et al. | 260/609 F |

FOREIGN PATENTS OR APPLICATIONS 2,304,962  8/1973  Germany .................. 260/609 F Primary Examiner—Lewis Gotts
Assistant Examiner—D. R. Phillips
Attorney, Agent, or Firm—Harry Falber

[57] ABSTRACT

New compounds of the following formula are described

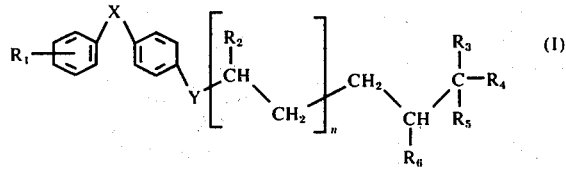

wherein
$R_1$ represents a hydrogen or halogen atom or a methyl radical,
$R_2$ represents a hydrogen atom or a methyl radical,
$R_3$ represents a hydrogen or halogen atom or a methyl or ethyl radical, and
$R_4$ represents a hydrogen or halogen atom or a methyl or $C_1$–$C_4$-alkoxy radical,
$R_5$ represents a hydrogen atom or a methyl radical, while
$R_6$ stands for a hydrogen atom, or
$R_5$ and $R_6$ together form a carbon-carbon bond,
X represents a sulphur atom or a sulphinyl, sulphonyl or sulphonyloxy group,
Y represents an oxygen atom or sulphur atom or an imino group, and
$n$ represents 0 or the number 1.

Processes for producing these compounds, as well as compositions and methods for pest control, using the new compounds as active substance.

11 Claims, No Drawings

DIPHENYL DERIVATIVES

The present invention relates to new 4-substituted derivatives of diphenyl sulphide, diphenyl sulphoxide, diphenyl sulphone and diphenyl sulphonate that are effective against pests, to processes for producing the new derivatives, as well as to compositions and processes for pest control using the new derivatives as active substances.

The new compounds of the invention correspond to the formula I

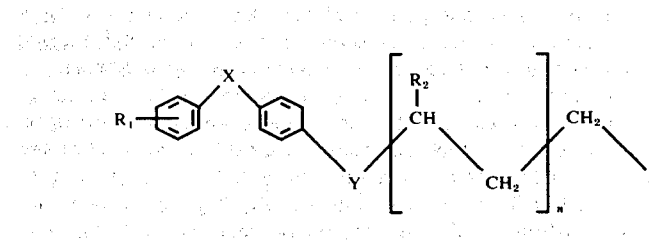

wherein
$R_1$ represents a hydrogen or halogen atom or a methyl radical,
$R_2$ represents a hydrogen atom or a methyl radical,
$R_3$ represents a hydrogen or halogen atom or a methyl or ethyl radical, and
$R_4$ represents a hydrogen or halogen atom or a methyl or $C_1$–$C_4$-alkoxy radical,
$R_5$ represents a hydrogen atom or a methyl radical, while
$R_6$ stands for a hydrogen atom, or
$R_5$ and $R_6$ together form a carbon-carbon bond,
X represents a sulphur atom or a sulphinyl, sulphonyl or sulphonyloxy group,
Y represents an oxygen atom or a sulphur atom or an imino group, and
$n$ represents O or the number 1.

Alkoxy radicals denoted by $R_4$ in the formula I are methoxy, ethoxy, n-propoxy, isopropoxy, n-butoxy, isobutoxy, sec.-butoxy and tert.-butoxy radicals; and by halogen atoms denoted by $R_1$, $R_3$ and $R_4$ are meant chlorine, fluorine, bromine and iodine atoms, especially chlorine and bromine atoms.

Compounds of the above-given formula I which are of particular interest on account of their action on pests, especially on insects, in particular on larvae and pupae of insects, and on members of the order Acarina, are those wherein $R_1$ represents hydrogen, p-methyl or p-chlorine,
$R_2$ represents a hydrogen atom or methyl,
$R_3$ represents a hydrogen atom or a methyl or ethyl radical,
$R_4$ represents a $C_1$–$C_3$-alkoxy radical, especially a methoxy or ethoxy radical,
$R_5$ represents a hydrogen atom or a methyl radical,
$R_6$ represents a hydrogen atom,
X represents a sulphur atom,
Y represents an oxygen atom, and
$n$ represents 0.

Particularly preferred among the aforementioned compounds of formula I are those wherein
$R_1$ represents a hydrogen atom,
$R_2$ represents a hydrogen atom or methyl,
$R_3$ and $R_5$ represent a hydrogen atom or methyl,
$R_4$ represents $C_1$–$C_3$-alkoxy, especially methoxy or ethoxy,
$R_6$ represents a hydrogen atom,
X represents a sulphur atom,
Y represents an oxygen atom, and
$n$ represents 0.

The compounds of the formula I are produced by the following methods known per se:

A. formation of the ether or thioether by condensation of a halide of the formula II

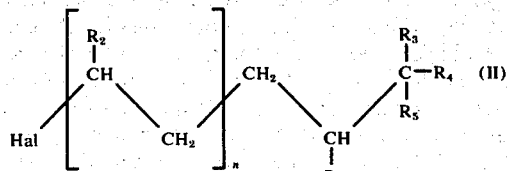

wherein Hal represents a chlorine, bromine or iodine atom, with a compound of the formula III

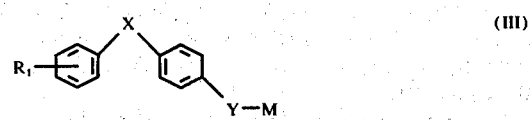

wherein M stands for a metal ion, especially a metal ion of the main group I or II of the periodic system, or for a hydrogen atom, in the presence of a base;

B. addition of an alcohol to a double bond by reaction of a compound of the formula Ib

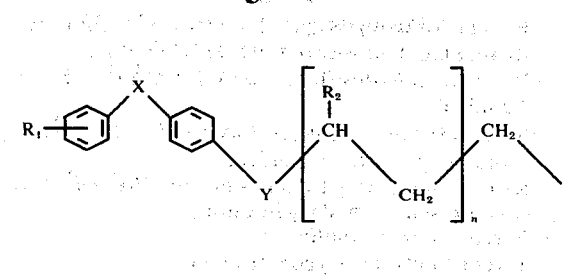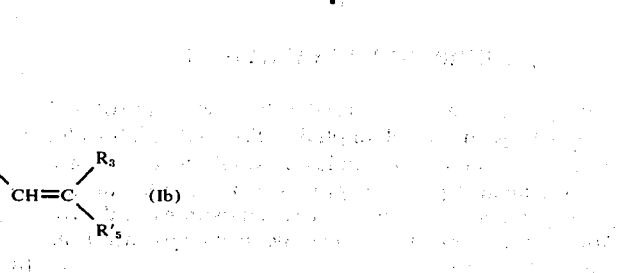

wherein $R'_5$ represents a hydrogen atom or a methyl radical, with a compound of the formula IV $$R'_4—OH \qquad (IV)$$

wherein $R'_4$ represents a $C_1$–$C_4$-alkyl radical in the presence of a mercury(II)-salt, and subsequent treatment of the resulting reaction product with a complex hydride in the presence of an alkali metal hydroxide and water.

In the formulae Ia, Ib, II and III above, the symbols $R_1$ to $R_6$, X, Y and n have the meanings given under formula I. The only compounds of the formula I obtainable by Process B are those wherein $R_4$ represents a $C_1$–$C_4$-alkoxy radical.

Depending on the reactivity of the applied halide of the formula II, the Process A can be performed in various solvents and at different reaction temperatures — always however in the presence of at least one mole of one of the bases mentioned below.

Suitable as solvents are, in particular, acetone, methyl ethyl ketone, cyclohexanone, 1,2-dimethoxyethane, tetrahydrofuran, dioxane, dialkyl ether, dimethylformamide, dimethylsulphoxide, hexamethylphosphoric acid triamide, sulpholane, inert hydrocarbons such as toluene, benzene, xylene and so forth. It is however possible to also use other solvents.

As necessary bases or acid acceptors in the case of ether formation from a compound of the formula II and a halide there are used, in particular, alkali metal hydroxides or alkaline-earth metal hydroxides, alkali metal carbonates or alkaline-earth metal carbonates, alkali metal hydrides or alkaline-earth metal hydrides and alkali metal alkoxides; it is however also possible to use organic bases, such as triethylamine or pyridine, as acid acceptors. The reaction temperatures for Process (A) are between −10° and 130°C, in most cases between 5 and 70° C (e.g. with the use of solvents such as dimethylsulphoxide, dimethylformamide, dioxane, sulpholane, tetrahydrofuran, hexamethylphosphoric acid triamide, 1,2-dimethoxyethane, etc.); or the reaction is performed at the boiling temperature of the employed solvent (e.g. in the case of ketones). The starting materials of the formulae II and III are known from the literature.

The reaction (B) to active substances of the formula I wherein $R_4$ represents a $C_1$–$C_4$-alkoxy radical is performed under normal pressure and in an anhydrous alcohol of the formula IV and, optionally, in an inert solvent or diluent, for example in ethers such as tetrahydrofuran, dioxane, diethyl ethers and 1,2-dimethyloxyethane.

In the 1st reaction step, the mercury(II)-salts used are preferably mercury(II)-acetate and mercury(II)-trifluoroacetate; and in the 2nd step, the complex hydride used is, e.g., an alkali metal boron hydride or alkaline-earth metal boron hydride. The reaction with the complex hydride is performed in the presence of an alkali metal hydroxide and water.

The reaction temperature for Process (B) is in the range of −10° C to +80° C, preferably between 0° and +25° C.

Some of the compounds of the formula I, e.g. such compounds wherein $R_2$ stands for a methyl radical and/or wherein $R_3$, $R_4$ and $R_5$ have unlike meanings, are present in different optically active isomers. If therefore in such cases in the production process no optically active starting materials are used, then there are necessarily obtained diastereomeric or racemic mixtures. Furthermore, if $R_5$ and $R_6$ together form a carbon-carbon bond, then there are normally obtained cis/trans mixtures of isomers as reaction products.

The mixtures of isomers can, e.g., be separated into the isomeric forms by means of chromatographical separation methods, e.g. by adsorption on a separating material having selective adsorption activity, such as silica gel or aluminium oxide, and subsequent elution of the separated isomers with a suitable solvent, e.g. diethyl ether, hexane, methyl acetate or ethyl acetate. A further chromatographical separation method is gas chromatography. In certain cases, a mixture of isomers can be separated also by fractional distillation or fractional crystallisation. It is understood that the present invention embraces both specific stereoisomers or cis/-trans isomers and the non-separated mixtures thereof.

The active substances of the formula I are suitable for the control of pests, especially for the control of insects, particularly larvae and pupae of insects, and members of the order Acarina.

Examples of families of insects and Acarina against which a good effect is exhibited are: Insects: Acrididae, Blattidae, Gryllidae, Gryllotalpidae, Tettigoniidae, Cimicidae, Pyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae, Acarina:

Ixodiade, Argasidae, Tetranychidae and Dermanyssidae.

Other biological active substances or compositions may be added to the described compositions of the invention. For the broadening of their sphere of action, the new composition can contain, in addition to the stated compounds of the general formula I, for example: insecticides, fungicides, bactericides, fungistatics, bacteriostatics or nematocides.

It is also to be pointed out that compounds of the formula I have a low toxicity to warm-blooded animals.

The compounds of formula I can be used on their own or together with suitable carriers and/or additives. Suitable carriers and additives may be solid or liquid, and they correspond to the substances common in formulation practice, such as natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The compositions according to the invention are produced in a manner known per se by the intimate mixing and/or grinding of active substances of formula I with suitable carriers, optionally with the addition of dispersing agents or solvents that are inert to the active substances. The active substances can be obtained and used in the following forms:

solid preparations:
 dusts, scattering agents, granulates, such as coated granulates, impregnated granulates and homogeneous granulates;

liquid preparations:

a.
 water-dispersible active-substance concentrates: wettable powders, pastes or emulsions,
b.
 solutions: aerosols.

The active substances of the formula I can be formulated, for example, as follows (parts denote parts by weight):

Dusts:
The following substances are used to produce (a) a 5% dust and (b) a 2% dust:
a.
 5 parts of active substance,
 95 parts of talcum;
b.
 2 parts of active substance,
 1 part of highly dispersed silicic acid,
 97 parts of talcum.
The active substances are mixed and ground with the carriers.

Granulate:
The following substances are used to produce a 5% granulate:
 5 parts of active substance,
 0.25 part of epichlorohydrin,
 0.25 part of cetyl polyglycol ether,
 3.50 parts of polyethylene glycol,
 91 parts of kaolin (particle size 0.3 –0.8 mm).
The active substance is mixed with epichlorohydrin and dissolved with 6 parts of acetone; the polyethylene glycol and cetyl polyglycol ether are then added. The solution thus obtained is sprayed on to kaolin, and the acetone is subsequently evaporated off in vacuo.

Wettable powder:
The following constituents are used in the preparation of (a) a 40% (b) and (c) a 25%, and (d) a 10% wettable powder:
a.
 40 parts of active substance,
 5 parts of sodium lignin sulphonate,
 1 part of sodium dibutyl-naphthalene sulphonate,
 54 parts of silicic acid;
b.
 25 parts of active substance,
 4.5 parts of calcium lignin sulphonate,
 1.9 parts of Champagne chalk/hydroxyethyl cellulose mixture (1:1),
 1.5 parts of sodium dibutyl naphthalene sulphonate,
 19.5 parts of silicic acid,
 19.5 parts of Champagne chalk,
 28.1 parts of kaolin;
c.
 25 parts of active substance,
 2.5 parts of isooctylphenoxy-polyoxyethylene-ethanol,
 1.7 parts of Champagne chalk/hydroxyethyl cellulose mixture (1:1),
 8.3 parts of sodium aluminium silicate, 16.5 parts of kieselguhr,
 46 parts of kaolin;
d.
 10 parts of active substance,
 3 parts of a mixture of the sodium salts of saturated fatty alcohol sulphates,
 5 parts of naphthalenesulphonic acid/formaldehyde condensate,
 82 parts of kaolin.

The active substances are intimately mixed, in suitable mixers, with the additives; the mixture is then ground in the appropriate mills and rollers. Wettable powders are obtained which can be diluted with water to give suspensions of any desired concentration.

Emulsifiable concentrates:
The following substances are used to produce (a) a 10%, (b) a 25% and (c) a 50% emulsifiable concentrate:
a.
 10 parts of active substance,
 3.4 parts of epoxidised vegetable oil,
 3.4 parts of a combination emulsifier consisting of fatty alcohol polyglycol ether and alkylarylsulphonate calcium salt,
 40 parts of dimethylformamide,
 43.2 parts of xylene;
b.
 25 parts of active substance,
 2.5 parts of epoxidised vegetable oil,
 10 parts of alkylarylsulphonate/fatty alcohol-polyglycol ether mixture,
 5 parts of dimethylformamide,
 57.5 parts of xylene;
c.
 50 parts of active substance,
 4.2 parts of tributylphenol-polyglycol ether,
 5.8 parts of calcium-dodecylbenzenesulphonate,
 20 parts of cyclohexanone,
 20 parts of xylene.

It is possible to prepare from these concentrates, by dilution with water, emulsions of any desired concentration.

Spray:
The following constituents are used to produce (a) a 5% spray and (b) a 95% spray:
a.
 5 parts of active substance,
 1 part of epichlorohydrin,
 94 parts of ligroin (boiling limits 160 – 190° C);
b.
 95 parts of active substance,
 5 parts of epichlorohydrin.

The following Examples serve to further illustrate the invention.

EXAMPLE 1

Production of 4-(3-methyl-2-butenyl-1-oxy)-diphenylsulphide 420 ml of a solution of 1N potassium hydroxide in ethanol is slowly added dropwise at room temperature to a solution of 77.6 g (0.38 mole) of 4-hydroxydiphenylsulphide and 56.6 g (0.38 mole) of 1-bromo-3-methyl-2-butene in 280 ml of anhydrous 1,2-dimethoxyethane. After the addition, the reaction mixture is stirred for a further 3 hours at room temperature. In the subsequent processing, the reaction solution is filtered off from the solid phase, and the filtrate is freed in vacuo from the solvent. The residue is dissolved in ether, the solution is washed 3 times with 10% potassium hydroxide solution and subsequently 4 times with saturated sodium chloride solution. After drying of the ether phase over sodium sulphate, the solvent is distilled off in vacuo and the oil obtained is chromatographed through silica gel with ethyl acetate:hexane = 1:10. There is obtained the product of the formula

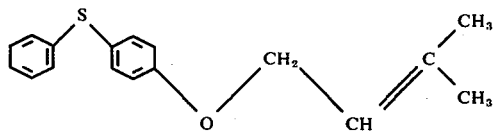

(Compound No. 1) as an oil having a refractive index of $n_D^{20} = 1.6010$.

EXAMPLE 2

Production of 4-(3-methyl-3-methoxy-butyl-1-oxy)-diphenylsulphide 20.25 g (0.075 mole) of 4-(3-methyl-2-butenyl-1-oxy)diphenylsulphide is added dropwise at room temperature in the course of 15 minutes to a suspension of 23.9 of mercury(II)-acetate in 75 ml of anhydrous methanol. After the addition, the reaction mixture is stirred for about 45 minutes at room temperature; there is then added dropwise, with ice-cooling, 75 ml of 3N sodium hydroxide solution. An addition is thereupon made dropwise of 75 ml of a 0.5N sodium borohydride solution in 3N sodium hydroxide solution, and the heterogeneous reaction mixture is stirred for 1½ hours at room temperature. In further processing, the reaction solution is filtered off from the precipitated mercury, and the solvent is removed in vacuo from the filtrate. The residue is dissolved in ether, and the solution is washed three times with saturated sodium chloride solution. After the drying of the ether phase with sodium sulphate, the solvent is distilled off in vacuo, and the oil obtained is chromatographed on silica gel with ethyl acetate/hexane = 1:10. There is obtained the product of the formula

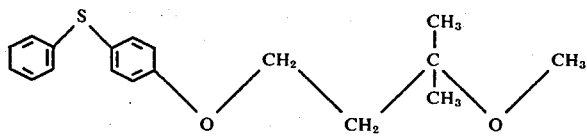

(Compound No. 2) as an oil with a refractive index of $n_D^{20} = 1.5785$.

EXAMPLE 3

The following compounds of the formula Ic are produced in a manner analogous to that of Examples 1 and 2

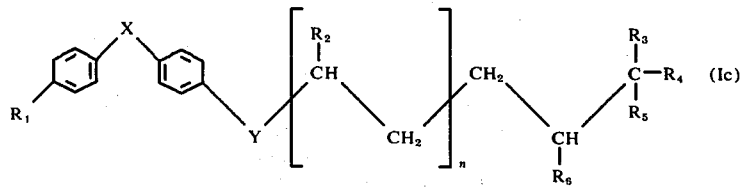

(cis/trans mixtures of isomers indicated by asterisks):

| Comp. No. | $R_1$ | $R_2$ | $R_3$ | $R_4$ | $R_5$ | $R_6$ | X | Y | n | Physical data |
|---|---|---|---|---|---|---|---|---|---|---|
| 3 | H |  | $CH_3-$ | $CH_3-$ | $-C-C-$ |  | S | S | 0 | $n_D^{20}$ 1,6393 |
| 4 | $CH_3-$ |  | $CH_3-$ | $CH_3-$ | $-C-C-$ |  | $\begin{matrix} O \\ \| \\ -S- \\ \| \\ O \end{matrix}$ | O | 0 | m.p. 107–109° C |
| 5 | H |  | $CH_3-$ | $CH_3-$ | $-C-C-$ |  | $\begin{matrix} -S- \\ \| \\ O \end{matrix}$ | O | 0 | m.p. 65–67° C |

-continued

| Comp No. | $R_1$ | $R_2$ | $R_3$ | $R_4$ | $R_5$ | $R_6$ | X | Y | Physical data |
|---|---|---|---|---|---|---|---|---|---|
| 6* | H | H | $CH_3-$ | | $-C-C-$ | S | O | O | $n_D^{20}$ 1.6063 |
| 7* | H | $C_2H_5-$ | $CH_3-$ | | $-C-C-$ | S | O | O | $n_D^{20}$ 1.5942 |
| 8* | H | $C_2H_5-$ | $CH_3-$ | | $-C-C-$ | S | $-NH-$ | O | $n_D^{20}$ 1.6135 |
| 9* | H | H | $CH_3-$ | | $-C-C-$ | S | S | O | $n_D^{20}$ 1.6285 |
| 10* | H | $C_2H_5$ | $CH_3-$ | | $-C-C-$ | S | S | O | $n_D^{20}$ 1.6171 |
| 11 | H | $CH_3-$ | $CH_3-$ | | $-C-C-$ | $\begin{array}{c}O\\\|\\-S-O-\\\|\\O\end{array}$ | O | O | $n_D^{20}$ 1.5518 |
| 12 | H | $CH_3-$ | $C_2H_5O-$ | $CH_3-$ | H | S | O | O | $n_D^{20}$ 1.5561 |
| 13* | H | H | Cl | | $-C-C-$ | S | O | O | $n_D^{20}$ 1.6205 |
| 14 | H | H | H | | $-C-C-$ | S | O | O | $n_D^{20}$ 1.6139 |
| 15 | H | $CH_3-$ | $\begin{array}{c}CH_3\\\diagdown\\ \phantom{CH}CH_2O\\\diagup\\CH_3\end{array}$ | | H | H | S | O | O | $n_D^{20}$ 1.5598 |
| 16 | H | $CH_3-$ | $CH_3O-$ | | H | H | S | O | O | $n_D^{20}$ 1.5803 |
| 17 | H | $CH_3-$ | $C_2H_5O-$ | | H | H | S | O | O | $n_D^{20}$ 1.5708 |
| 18 | H | $CH_3-$ | $CH_3O-$ | | H | H | $\begin{array}{c}O\\\|\\-S-\end{array}$ | O | O | |

| Comp. No. | $R_1$ | $R_2$ | $R_3$ | $R_4$ | $R_5$ | $R_6$ | X | Y | n | Physical data |
|---|---|---|---|---|---|---|---|---|---|---|
| 19 | H | | $CH_3-$ | $CH_3-$ | | $-C-C-$ | S | O | O | $n_D^{20}$: 1.6010 |
| 20 | H | | $CH_3-$ | $CH_3O-$ | $CH_3-$ | H | S | O | O | $n_D^{20}$: 1.5785 |
| 21* | Cl | | H | $CH_3-$ | | $-C-C-$ | S | O | O | 74 - 75° C |
| 22 | Cl | | $CH_3-$ | $CH_3O-$ | H | H | S | O | O | $n_D^{20}$: 1.5887 |
| 23 | Cl | | $CH_3-$ | $C_2H_5O-$ | H | H | S | O | O | $n_D^{20}$: 1.5778 |
| 24* | $CH_3-$ | | H | $CH_3-$ | | $-C-C-$ | S | O | O | m.p. 46 - 47° C |
| 25 | $CH_3-$ | | $CH_3-$ | $-OCH_3$ | H | H | S | O | O | $n_D^{20}$: 1.5748 |
| 26 | $CH_3-$ | | $CH_3-$ | $-OC_2H_5$ | H | H | S | O | O | $n_D^{20}$: 1.5672 |
| 27* | H | $CH_3-$ | $CH_3-$ | $CH_3-$ | | $-C-C-$ | S | O | 1 | $n_D^{20}$: 1.5556 |

EXAMPLE 4

A. Contact action on Dysdercus-fasciatus larvae

A specific amount of a 0.1% acetonic active-substance solution (corresponding to 10 mg of active substance per square metre) was transferred by pipet to an aluminum dish and uniformly distributed. After evaporation of the acetone, 10 larvae in the 5th stage of Dysdercus fasciatus were placed into the treated dish containing feed and moist cotton wool. The dish was then covered with a perforated lid. After about 10 days, i.e. as soon as the control insects had moulted into adults, the test insects were examined to determine the number of normal adults.

Compounds 1 to 27 exhibited a good action in the above test.

B. Contact action on Aedes-aegypti larvae

About 20 two-day-old larvae of the yellow-fever mosquito (Aedes aegypti) were placed in position in a breaker containing a solution of the active substance (concentration 5 ppm). The breaker was then covered with a perforated lid. After the control insects had moulted into adults, the test insects were examined and the percentage of normal adults in comparison with the control adults was determined.

Compounds 1 to 27 exhibited a good action in the above test.

C. Contact action on Tenebrio-molitor pupae

A specific amount of a 0.1% acetonic active-substance solution corresponding to 10 mg of active substance per square metre was transferred by pipet into an aluminium dish and uniformly distributed. After evaporation of the acetone, 10 freshly formed pupae were placed onto the treated surface, and the dish was covered with a perforated lid. After the control insects had left the cocoon as imagines, the test insects were examined to determine the number of normal adults.

Compounds 1 to 27 exhibited a good action in the above test.

EXAMPLE 5

A. Action against Musca domestica

An amount in each case of 50 g of CSMA maggot substrate was weighed off in beakers. For each active substance, 2.5 ml of a 1% acetonic solution of the respective substance was transferred by pipet twice to 50 g of maggot substrate each time. After a thorough mixing of the treated substrate, the solvent was allowed to evaporate off. There were then deposited per active substance in each case 25 one-, two- and three-day-old maggots and about 50 fly eggs. After completion of pupation, the pupae were flushed out and counted. After a period of 10 days, the number of emerged flies was counted and hence any effect on metamorphosis was established.

Compounds 1 to 27 exhibited in this test a good action on Musca domestica.

B. Action against Ephestia kuhniella 50 g of wheat flour was made up in two beakers with a specific amount of active substance to give a 5% dust, the concentration being 0.05%. Into each beaker (25 g of flour) there were placed 10 larvae of Ephesta kuhniella. The pattern of population was ascertained over a period of 8 weeks and the number of moths determined.

Compounds 1 to 27 exhibited in this test a good action on Ephestia kuhniella.

EXAMPLE 6

Action against red spider mites

Phaseolus vulgaris (bush beans) were infested, 12 hours before the test for acaricidal action, with an infested piece of leaf from a mass culture of Tetranychus urticae. The transferred mobile stages were sprayed with the emulsified test preparations, at a concentration of 0.04%, by means of a chromatographysprayer in a manner ensuring no running-off of the spray liquor. An assessment was made after 2 to 7 days, by examination under a binocular, of the living and of the dead larvae, adults and eggs, and the results were expressed in percentages. The treated plants were kept during the holding time in greenhouse compartments at 25° C.

Compounds 1 to 27 exhibited in the above test a good action on eggs, larvae and adults of Tetranychus urticae.

We claim:
1. A compound of the formula I

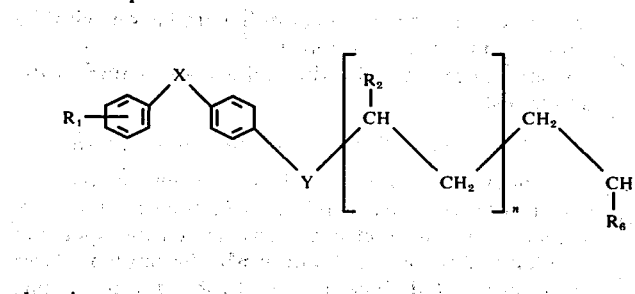

wherein
 $R_1$ represents a hydrogen or halogen atom or a methyl radical,
 $R_2$ represents a hydrogen atom or a methyl radical,
 $R_3$ represents a hydrogen or halogen atom or a methyl or ethyl radical, and
 $R_4$ represents a hydrogen or halogen atom or a methyl or $C_1$–$C_4$-alkoxy radical,
 $R_5$ represents a hydrogen atom or a methyl radical, while
 $R_6$ stands for a hydrogen atom, or
 $R_5$ and $R_6$ together form a carbon-carbon bond,
 X represents a sulphur atom,
 Y represents an oxygen atom, and
 $n$ represents O or the number 1.

2. The compound according to claim 1 wherein
 $R_1$ represents a hydrogen atom, p-methyl or p-chlorine,
 $R_3$ represents a hydrogen atom, methyl or ethyl,
 $R_4$ represents a $C_1$–$C_3$-alkoxy radical,
 $R_5$ represents a hydrogen atom or methyl,
 $R_6$ represents a hydrogen atom, and
 $n$ represents 0.

3. The compound according to claim 1 wherein
 $R_1$ represents a hydrogen atom,
 $R_3$ and $R_5$ represent a hydrogen atom or methyl,
 $R_4$ represents $C_1$–$C_3$-alkoxy,
 $R_6$ represents a hydrogen atom, and
 $n$ represents 0.

4. The compound according to claim 2 characterised in that $R_4$ represents a methoxy or ethoxy radical.

5. 4-(3-Methoxy-butyl-1-oxy)-diphenylsulphide according to claim 3.

6. 4-(3-Ethoxy-butyl-1-oxy)-diphenylsulphide according to claim 3.

7. 4-(3-i-propoxy-butyl-1-oxy)-diphenylsulphide according to claim 2.

8. 4-(3-Methyl-3-methoxy-butyl-1-oxy)-diphenylsulphide according to claim 3.

9. 4-(3-methyl-3-ethoxy-butyl-1-oxy)-diphenylsulphide according to claim 3.

10. A insect or acarid control composition containing as active constituent a insecticidally or acaridicidally effective amount of a compound according to claim 1 of the formula I:

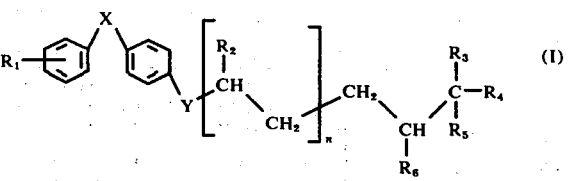

wherein
 $R_1$ represents a hydrogen or halogen atom or a methyl radical,
 $R_2$ represents a hydrogen atom or a methyl radical,
 $R_3$ represents a hydrogen or halogen atom or a methyl or ethyl radical, and
 $R_4$ represents a hydrogen or halogen atom or a methyl or $C_1$–$C_4$-alkoxy radical,
 $R_5$ represents a hydrogen atom or a methyl radical, while
 $R_6$ stands for a hydrogen atom, or
 $R_5$ and $R_6$ together form a carbon-carbon bond,
 X represents a sulphur atom,
 Y represents an oxygen atom, and
 $n$ represents O or the number 1;
together with a suitable carrier therefor.

11. A method for combatting insects or acarids which comprises applying to said insects or acarids or the locus thereof a insecticidally or acaridicidally effective amount of a compound according to claim 1 of the formula I:

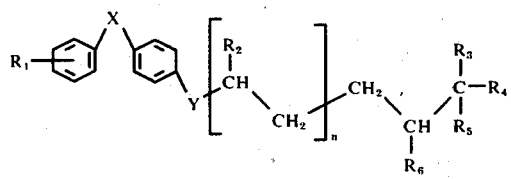

wherein $R_1$ represents a hydrogen or halogen atom or a methyl radical,
$R_2$ represents a hydrogen atom or a methyl radical,
$R_3$ represents a hydrogen or halogen atom or a methyl or ethyl radical, and
$R_4$ represents a hydrogen or halogen atom or a methyl or $C_1$–$C_4$-alkoxy radical,
$R_5$ represents a hydrogen atom or a methyl radical, while
$R_6$ stands for a hydrogen atom, or
$R_5$ and $R_6$ together form a carbon-carbon bond,
X represents a sulphur atom,
Y represents an oxygen atom, and
$n$ represents O or the number 1.

* * * * *

UNITED STATES PATENT AND TRADEMARK OFFICE
CERTIFICATE OF CORRECTION

PATENT NO. : 3,998,972
DATED : December 21, 1976
INVENTOR(S) : Saleem Farooq, et al It is certified that error appears in the above-identified patent and that said Letters Patent are hereby corrected as shown below:

In the heading under Foreign Application Priority Data please add

-- October 14, 1974   Switzerland   13757/74 --

Signed and Sealed this

Thirteenth Day of September 1977

[SEAL]

Attest:

RUTH C. MASON
*Attesting Officer*

LUTRELLE F. PARKER
*Acting Commissioner of Patents and Trademarks*